(12) United States Patent
Sander

(10) Patent No.: US 8,511,825 B2
(45) Date of Patent: Aug. 20, 2013

(54) ILLUMINATING DEVICE FOR AN OPERATING MICROSCOPE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 264 days.

(21) Appl. No.: 13/091,942

(22) Filed: Apr. 21, 2011

(65) Prior Publication Data

US 2011/0261322 A1    Oct. 27, 2011

(30) Foreign Application Priority Data

Apr. 23, 2010    (DE) .......................... 10 2010 028 169

(51) Int. Cl.
*A61B 3/10*    (2006.01)

(52) U.S. Cl.
USPC ............................ 351/216; 351/214; 351/221

(58) Field of Classification Search
USPC ................. 351/214, 216, 220, 221; 359/389, 359/385
See application file for complete search history.

(56) References Cited

U.S. PATENT DOCUMENTS

| 5,098,426 | A | 3/1992 | Sklar et al. |
| 5,428,414 | A * | 6/1995 | Iwane ............................ 351/214 |
| 7,142,359 | B2 | 11/2006 | Sander |
| 8,177,364 | B2 * | 5/2012 | Reimer et al. ................. 351/221 |
| 2004/0143246 | A1 | 7/2004 | Maeda et al. |

FOREIGN PATENT DOCUMENTS

| DE | 4326761 A1 | 2/1995 |
| DE | 19644662 A1 | 4/1998 |
| EP | 0661020 B1 | 5/2001 |

* cited by examiner

*Primary Examiner* — Hung Dang
(74) *Attorney, Agent, or Firm* — Patentbar International, P.C.

(57) ABSTRACT

The present invention relates to an Illuminating device for an operating microscope in ophthalmic surgery, having at least one light source (151), at least one lens (152, 155), at least one luminous field diaphragm (153), and at least one optical deflector (156), wherein in order to provide an illumination beam path (119) light from the light source (151) is guided through a main objective (107) which is disposed between the deflector (156) and an eye (180) that is to be observed, and on to the eye that is to be observed, wherein a device (154) that can be introduced into the illumination beam path (119) for acting upon the illumination beam path (119) with a structure that comprises transparent and non-transparent or opaque regions such that this structure can be imaged on or close to the retina (180*b*) of the eye (180) that is to be observed.

23 Claims, 3 Drawing Sheets

ILLUMINATING DEVICE FOR AN OPERATING MICROSCOPE

CROSS-REFERENCE TO RELATED APPLICATIONS

This application claims priority to German Patent Application No. DE 10 2010 028 169.7 filed on Apr. 23, 2010, that is incorporated herein by reference in its entirety.

FIELD OF THE INVENTION

The present invention relates to an illuminating device for an operating microscope, particularly in ophthalmic surgery, according to the preamble of claim 1.

BACKGROUND OF THE INVENTION

When operating microscopes are used in eye surgery, particularly in cataract removal, the angle between the illumination axis and the observation axis of the microscope should be kept as small as possible. The advantage of this type of illumination is that the rays of light falling perpendicularly onto the eye are reflected diffusely by the retina and as a result the lens capsule of the eye appears as a translucent reddish colour. This effect is also known as the red reflex. The quality of this red reflex is of critical importance in cataract removal. In this operation, after the lens has been removed, all tissue residues also have to be removed from the eye. This can only be done successfully if these tissue residues are shown up with sufficient optical contrast, and this is the purpose for which the red reflex is used.

However, in the course of a typical operation, not only is it essential to show the red reflex, but there must also be conventional illumination (as required) to illuminate the operating area.

From EP 0 661 020 B1, an illuminating device for an operating microscope is known, having at least one light source, a collector lens system of a luminous field diaphragm or aperture, optical deflectors, other lenses and a main objective, the illuminating light being guided through the main objective into the object plane. The luminous field diaphragm is imaged through the deflectors and the lenses are imaged through the main objective into the object plane. Moreover, to produce red reflex illumination, switchable means are provided in the illumination beam path which store the image of the luminous field diaphragm and image the light source into the object plane.

From DE 4 326 761 a stereomicroscope for ophthalmic surgery is known, for high-contrast visualisation of transparent media in the reflected transmitted light, wherein phase contrast elements are arranged in the two observation beam paths which image transparent media as phase objects with amplitude contrast. The provision and positioning of phase contrasting elements of this kind is regarded as laborious.

One particularly disadvantageous aspect of phase contrast observation of this kind is that the phase contrasting elements typically configured as diaphragms (apertures) have to be introduced into the observation beam of the microscope. Expediently, positions are provided for this purpose at which the first orders of refraction of the secondary scattered light source produce the image. It is difficult to achieve sufficiently accurate positioning with the complex illumination and imaging processes, including the patient's eyes that are to be observed, which may vary greatly both in terms of dimensions and nature.

The provision of different diaphragm shapes and sizes using LCD (liquid crystal device) with individually controllable pixels is known from DE 196 44 662 A1, although this publication does not describe any applications in ophthalmic surgery.

SUMMARY OF THE INVENTION

The problem of the present invention is to provide an operating microscope for ophthalmic surgery with which it is easy to provide good contrast in the use of a red reflex display, e.g. for removing tissue residues from the eye.

It should be noted that the stereomicroscope according to the invention can also be used in fields other than ophthalmic surgery, namely wherever transparent objects are to be visualised with maximum contrast in reflected transmitted light.

The solution according to the invention is particularly characterised in that the observation beam paths in the operating microscope are left substantially unchanged, i.e. unlike in phase contrasting absolutely no information or light intensity is lost, for example as the result of the exclusion of higher orders of diffraction. All modifications or manipulations of the light conditions take place in the illumination beam path.

According to the invention the structure comprising transparent and non-transparent regions is imaged on or close to the retina of the eye under observation. Regarding the term "close to" it should be noted that in practice it is found that exact imaging on the retina is not necessary to produce the effects according to the invention. Images with a focal point just in front of or just behind the retina also lead to the effects according to the invention. This also takes account of the fact that eyes under examination have physiological differences from one another, so that precise imaging on the retina may be a very tricky process. Thus, the term "close to" should be taken to mean, in particular, imaging with +/−10 dioptres (dpt).

It is particularly pointed out that the illuminating device according to the invention is configured as an incident-light illuminating device. Conventional transmitted-light illuminating devices cannot be used to illuminate the retina in operating microscopes for eye surgery, as the eye cannot be taken out of the eye-socket for an operation and moreover the retina is opaque.

Advantageous embodiments of the invention are the subject of the sub-claims.

Preferably, the device for acting on the illumination beam path with a structure having transparent and non-transparent or opaque regions is configured as a diaphragm (aperture) and/or lens and/or deflector. Particularly preferably, the device is configured as a further diaphragm (in addition to the luminous field diaphragm) which can be positioned for example between the optical deflector and the light source, particularly between the deflector and the luminous field diaphragm. It would also be possible to provide the device on one of the lenses used in the illuminating device and/or on the deflector, for example to apply corresponding structures by painting or vapour deposition.

Particularly preferably, the structure has regularly and/or irregularly repeating structural elements, particularly structural elements that repeat at least three times. Combinations of regularly and irregularly repeating structural elements are also possible. Such structures may be optimally adapted to certain illuminating conditions or ophthalmological requirements, and in particular it is also possible to equip an illuminating device according to the invention with different devices that can be selectively introduced into the illumination beam path.

It is particularly preferable for the structure to be configured as a pattern with concentric circles and/or comprising a grid pattern and/or chequerboard design. Regular structures of this kind produce particularly good contrast representation.

It is also advantageously possible to provide the structure using an MMA (micromirror array), MEM (microelectromagnetic mirrors) or SLM device (spatial light modulator), particularly using OLEDs, LEDs, displays, etc. Devices of this kind allow the particularly flexible provision of structures, i.e. in a manner that can be varied to suit specific requirements.

Expediently, the deflector provides 0° illumination or 2° illumination. These types of illumination, i.e. illumination beam paths incident at a very small angle of incidence relative to the optical axis of the main objective, prove particularly favourable for producing the red reflex.

The deflector used in this context is expediently configured as a deflecting prism or partly translucent or semi-translucent mirror.

It has proved advantageous to make the illuminating device capable of being switched on and off, the deflector in particular being capable of being taken out of the observation beam path altogether. This makes it possible in particular to provide an unobstructed additional illumination of the object or eye that is to be observed, in which the illuminating device according to the invention is totally removed from the observation beam paths.

According to another particularly preferred embodiment, the illuminating device according to the invention comprises a beam splitter for splitting the illumination beam path into two partial beam paths, each partial beam path having an associated deflector. This measure makes it possible to provide simultaneous illumination from different angles, also known as stereoscopic illumination, each of the partial beam paths being acted upon by the structure having transparent and non-transparent regions. As a result, overlapping or interfering patterns can be displayed on the retina, thus enabling variable patterns to be produced on the retina using only a device for acting upon the illumination beam path with one structure, by slightly varying the deflection angles of the deflectors, and/or the orientation of the beam splitter, for example.

The illuminating device according to the invention provides overall an incident-light illumination, the illuminating light of which, by reflection on the retina, provides a combination of a red reflex and dark field illumination in the transmitted light.

The method according to the invention is characterised by the introduction into an illumination beam path of a device for imaging a structure that comprises transparent and non-transparent or opaque regions onto or close to the retina of the eye that is to be observed. With the method according to the invention, particularly effective illumination for high-contrast representation of the red reflex is provided.

According to the invention, a method of contrasting transparent media in the human eye in transmitted light is also provided, which is characterised by the imaging of a structure formed in an illumination beam path comprising transparent and non-transparent or opaque regions onto or close to the retina of the eye that is to be observed, in order to provide a structured red reflex. The structured red reflex provided according to the invention is made up of a combination of a red reflex and dark field illumination, the red reflex regions corresponding to the transparent regions, and the dark field illumination areas corresponding to the non-transparent or opaque regions of the structure imaged on or close to the retina. Tissue residues left behind in the eye when a lens is removed can be displayed with optical contrast particularly at the transitional areas between the red reflex regions and dark field illumination regions.

BRIEF DESCRIPTION OF THE DRAWINGS

The invention will now be described in more detail with reference to the attached drawings, wherein.

DETAILED DESCRIPTION OF THE PREFERRED EMBODIMENTS

Figure 1:
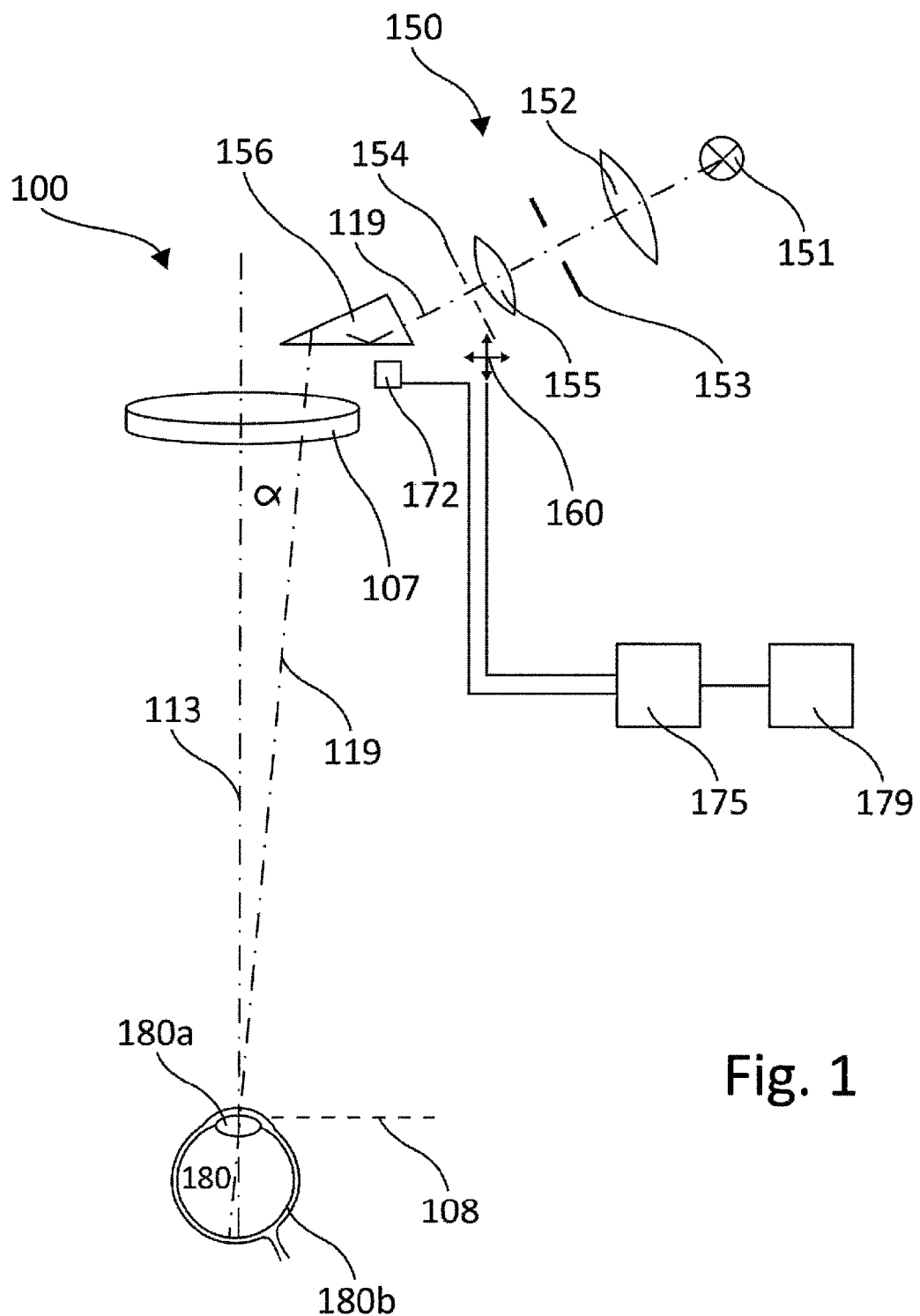
FIG. 1 shows a first preferred embodiment of an illuminating device according to the invention shown in lateral sectional view.

A microscope that comprises a first preferred embodiment of the illuminating device according to the invention is shown purely schematically in FIG. 1 and generally designated 100. The only optical component of the microscope specifically shown is the main objective 107. An illuminating device is generally designated 150. It comprises a light source 151, a collector lens system 152, a luminous field diaphragm (aperture) 153, other lenses shown schematically and designated 155 and a deflecting prism 156 serving as a deflector. An additional element is a further diaphragm (aperture) 154 provided between the luminous field diaphragm 153 and the deflecting prism 156. This diaphragm 154 for the purposes of the present invention represents a device for acting upon an observation beam path with a structure, and is explained in detail hereinafter.

An illumination beam path 119 is passed from the light source 151 through the collector lens system 152, the luminous field diaphragm 153, the further lenses 155, the diaphragm 154 and the deflecting prism 156 through the main objective 107 onto an eye 180 that is to be observed. The beam path 119 shown is configured here as a Köhler illumination beam path, by way of example. The luminous field diaphragm 153 is imaged, through the components downstream of it, in an object plane 108 in which the lens 180a with the lens capsule of the eye 180 is arranged.

The luminous field diaphragm 153 images a luminous field boundary with a sharp edge into the plane 108.

The additional diaphragm 154 has a patterning or structure (unlike the diaphragm 153). This structure may take the form of a pattern with periodically repeating structural elements and/or irregularly repeating structural elements. The patterns may comprise, for example, parallel lines, concentric circles or chequerboard structures. Preferred structures or patterns are described below.

These patterns applied to the diaphragm 154 are imaged not in the plane 108 but on the retina 180b of the eye 180.

The diaphragm 154 can be moved parallel and perpendicularly to the illumination beam path 119 by means of an adjusting mechanism designated 160 that is schematically shown by double arrows. As a result of the parallel adjustment, the diaphragm 154 can be adapted to fit the biological conditions (for example the dimensions) of the eye 180 so as to ensure that a sharp image can be provided on the retina 180b. The adjustment of the diaphragm 154 may be carried out automatically if the biometric data of the eye are available and can be called up. For this purpose, a data memory 179 may be provided, for example, which cooperates with a sensor 172 and an evaluating and control unit 175. For example, the data relating to an eye that are stored in the data memory 179 may be made available to the evaluating and control unit 175, while the sensor 172 measures the sharpness of the image on the retina and also provides this information to the evaluating and control unit 175. On the basis of this combination of stored data and measured values, the diaphragm 154 can be positioned particularly rapidly. However, it is also possible to carry out adjustment of the diaphragm 154 solely on the basis of stored data, i.e. without using the sensor 172. In the same way it is possible to adjust the diaphragm 154 without using stored data, and solely using the information from the sensor 172.

Possible adjustability of the diaphragm 154 perpendicularly to the axis of the illumination beam path 119 is described below.

It will be realised that after deflection through the deflecting prism 156 and passage through the main objective 107 the illumination beam path 119 is at an angle relative to the optical axis 113 of the main objective 107.

The illumination beam path 119 as a whole passes through the object plane 108 onto the retina 180b of the eye and generates a red reflex by scattering and reflection.

Compared with conventional solutions, the solution according to the invention is characterised in that the structure or patterning of the diaphragm 154 is imaged on the retina 180b. This imaging of the structure of the diaphragm 154 on the retina 180b results in a very good, i.e. high-contrast, representation for example of capsulorrhexis (removal of the lens capsule in a cataract operation), the quality of this representation depending in particular on the size (respective areas and sides) of the transitions of the illumination images on the retina.

In all, thanks to the structured illumination which represents 0° or 2° illumination thanks to the ability of the deflecting prism 156 to be positioned close to the optical axis 113, areas that reflect as red (diffuse) and non-reflecting, i.e. black, areas are obtained on the retina. Particularly at the transitions between red and black areas on the retina, blurred transitions are obtained, so that for example residues of the lens on the posterior lens capsule close to the plane 108 may luminesce against a black background and be perceived by an observer. Thus a partial dark field illumination is obtained in the transmitted light thanks to the incident light provided by the light source 151.

Figure 2:
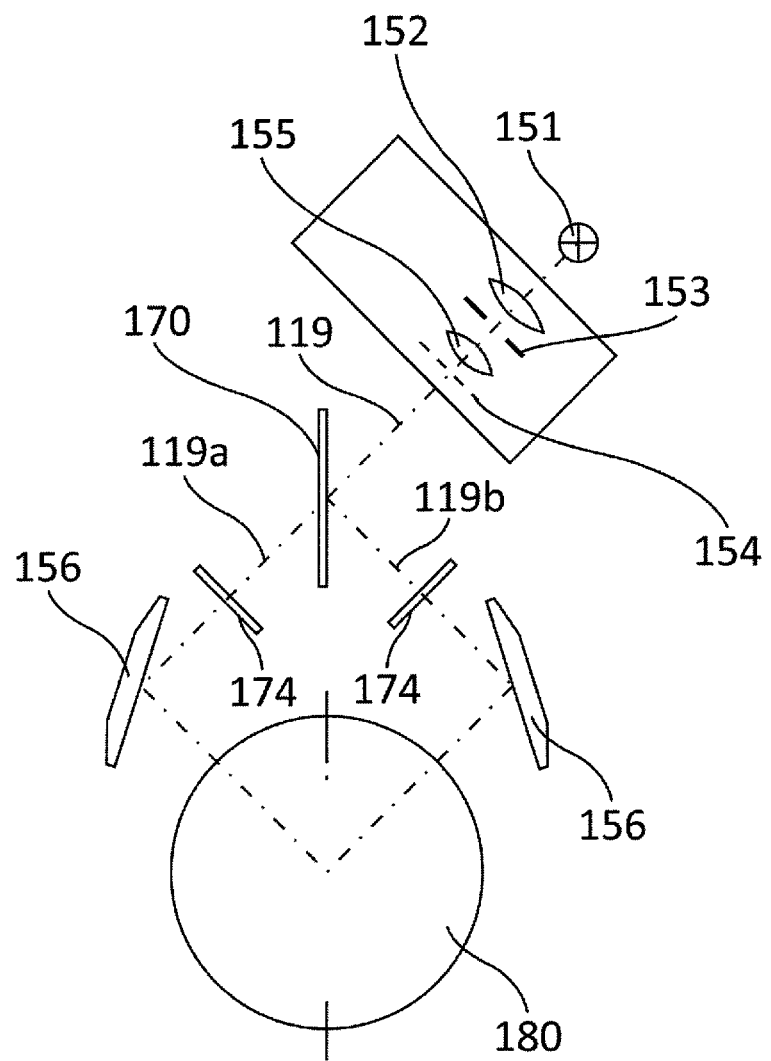
FIG. 2 shows a second preferred embodiment of an illuminating device according to the invention in schematic plan view.

A further development of this idea is shown in FIG. 2. Identical or similar components have the same reference numerals. The embodiment in FIG. 2 is distinguished from the embodiment in FIG. 1 in that a beam splitter 170 is provided between the diaphragm 154 having a structure and the two deflectors 156 according to this embodiment. This beam splitter causes the illumination beam path 119 to split into two partial beam paths 119a, 119b. Optionally, filter elements 174 are formed between the beam splitter 170 and the deflectors 156.

The two partial beam paths 119a, 119b illuminate the retina of the eye 180 (not shown here) as shown previously with reference to FIG. 1. The special feature of this embodiment is that thanks to the two partial beam paths 119a, 119b two overlapping and interfering patterns can be represented on the retina, which can be altered by varying the position or orientation of the beam splitter 170 and/or the deflectors 156. This is an additional possibility for optimising the generation of contrast, as it can be used to move the above-mentioned red and black areas on the retina in a simple manner, for example continuously.

Moreover, in both embodiments, it is additionally possible to achieve an additional improvement in contrast by deliberate defocusing of the illuminating images of the diaphragm 154 on the retina. The embodiments according to FIGS. 1 and 2 are characterised in that, with a diaphragm in the primary illumination beam path 119, a structured secondary illumination is produced on the retina 180b, the structure of which is not visible in the primary illumination, i.e. in the plane 108, and thus does not inconvenience the observer. The solution according to the invention provides the possibility of arranging the illuminating device above the main objective 107 using deflector means, for example the deflecting prism 156, thus providing a so-called integrated illumination. According to the invention no special phaco diaphragms with special adjusting means are required and furthermore there is no loss of light or loss of information as a result of diaphragms of this kind in the observation beam paths. The manipulating, contrast-improving interventions are carried out only in the illumination beam path according to the invention.

The diaphragm 154 may advantageously take the form of an MEM or SLM the control of which can be used in conjunction with the optimum displacement by calculation in the biometric data in the control unit to carry out a calculation for optimum shaping.

FIGS. 3a-3d show examples of structures that may be used according to the invention. As already mentioned, these structures may be produced for example by means of or on the diaphragm 154, the deflectors 156, or on other optical components such as the lenses 152, 155 or the beam splitter 170.

Figure 3A:
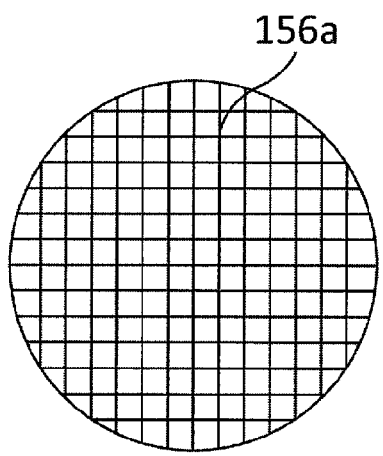
FIGS. 3a-3d show preferred embodiments of structures that can be introduced into the illumination beam path or imaged on a secondary light source, e.g. the fundus of an eye (retina).

FIG. 3a shows a grid-like structure, while the individual grid lines 156a may also be made broader.

Figure 3B:
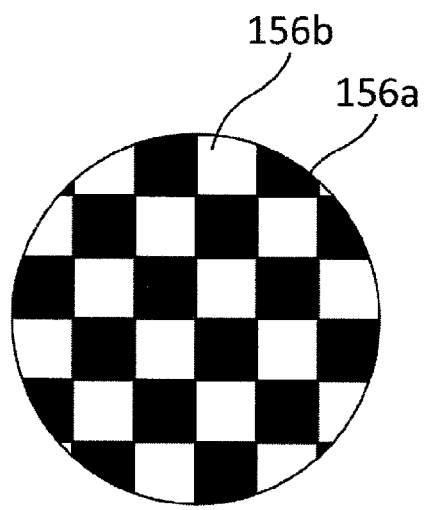

FIG. 3b shows a structure with chequerboard pattern elements 156a, 156b, while the length of the sides of the elements may be chosen freely.

Figure 3C:
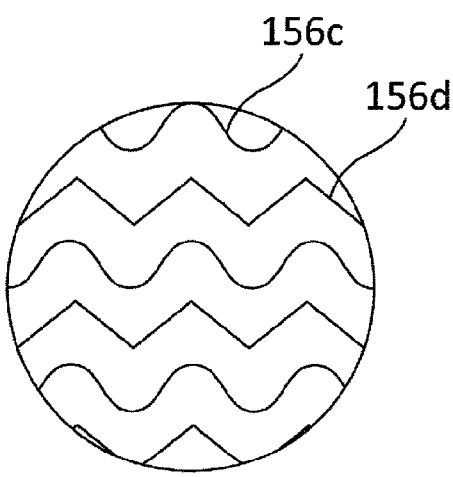

FIG. 3c shows a structure with wavy structural elements 156c or zig-zag-shaped structural elements 1156d. Naturally, these structural elements may also be used on their own or in other combinations.

Figure 3D:
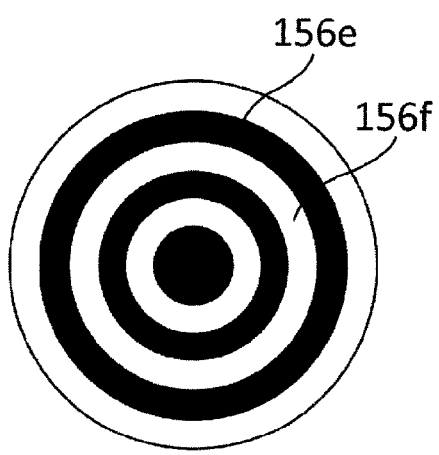

FIG. 3d finally shows a structure with concentric circles 156e, 156f.

The areas shown in black in FIGS. 3a-3d may be totally non-transparent or opaque, and the elements shown in white may be totally transparent. However, it is also possible to use or form semitransparent elements. It is possible, in particular, to provide smooth transitions from transparent to opaque between the individual structural elements, in which the transparency conforms to a sinusoidal configuration.

What is claimed is:

1. An illuminating apparatus for an operating microscope in ophthalmic surgery, comprising:
at least one light source,
at least one lens,
at least one luminous field diaphragm, and
at least one optical deflector,
wherein, in order to provide an illumination beam path, light from the light source is guided through a main objective disposed between the deflector and an eye that is to be observed, and onto the eye that is to be observed,
and further comprising a device that can be introduced into the illumination beam path for acting upon the illumination beam path with a structure that comprises transparent and non-transparent or opaque regions such that this structure can be imaged on or close to a retina of the eye that is to be observed;

wherein the structure is configured as a pattern with concentric circles or comprises a grid pattern and/or checkerboard pattern elements.

2. The illuminating apparatus of claim 1, wherein the device is a diaphragm and/or lens and/or deflector.

3. The illuminating apparatus of claim 1, wherein the structure comprises regularly and/or irregularly repeating structural elements, particularly structural elements that repeat at least three times.

4. The illuminating apparatus of claim 1, wherein the structure is provided by an MMA, MEM or SCM device, particularly using OLEDs, LEDs or displays.

5. The illuminating apparatus of claim 1, wherein the deflector provides a 0° illumination or a 2° illumination.

6. The illuminating apparatus of claim 1, wherein the deflector is a deflecting prism or a partly transparent or semitransparent mirror.

7. The illuminating apparatus of claim 1, which provides incident-light illumination, the illuminating light of which provides, by reflection on the retina, a combination of a red reflex and a dark field illumination in transmitted light.

8. An illuminating apparatus for an operating microscope in ophthalmic surgery, comprising:
   at least one light source,
   at least one lens,
   at least one luminous field diaphragm, and
   at least one optical deflector,
   wherein, in order to provide an illumination beam path, light from the light source is guided through a main objective disposed between the deflector and an eye that is to be observed, and onto the eye that is to be observed,
   further comprising a device that can be introduced into the illumination beam path for acting upon the illumination beam path with a structure that comprises transparent and non-transparent or opaque regions such that this structure can be imaged on or close to a retina of the eye that is to be observed;
   wherein the apparatus can be switched on and off, and the deflector is capable of being removed entirely from an observation beam path.

9. The illuminating apparatus of claim 8, wherein the device is a diaphragm and/or lens and/or deflector.

10. The illuminating apparatus of claim 8, wherein the structure comprises regularly and/or irregularly repeating structural elements, particularly structural elements that repeat at least three times.

11. The illuminating apparatus of claim 8, wherein the structure is provided by means of an MMA, MEM or SCM device, particularly using OLEDs, LEDs or displays.

12. The illuminating apparatus of claim 8, wherein the deflector provides a 0° illumination or a 2° illumination.

13. The illuminating apparatus of claim 8, wherein the deflector is a deflecting prism or a partly transparent or semitransparent minor.

14. The illuminating apparatus of claim 8, which provides incident-light illumination, the illuminating light of which provides, by reflection on the retina, a combination of a red reflex and a dark field illumination in transmitted light.

15. An illuminating apparatus for an operating microscope in ophthalmic surgery, comprising:
   at least one light source,
   at least one lens,
   at least one luminous field diaphragm, and
   at least one optical deflector,
   wherein, in order to provide an illumination beam path, light from the light source is guided through a main objective disposed between the deflector and an eye that is to be observed, and onto the eye that is to be observed,
   further comprising a device that can be introduced into the illumination beam path for acting upon the illumination beam path with a structure that comprises transparent and non-transparent or opaque regions such that this structure can be imaged on or close to a retina of the eye that is to be observed;
   and further comprising a beam splitter for splitting the observation illumination beam path into two partial beam paths, each partial beam path having an associated deflector.

16. The illuminating apparatus of claim 15, wherein the device is a diaphragm and/or lens and/or deflector.

17. The illuminating apparatus of claim 15, wherein the structure comprises regularly and/or irregularly repeating structural elements, particularly structural elements that repeat at least three times.

18. The illuminating apparatus of claim 15, wherein the structure is provided by means of an MMA, MEM or SCM device, particularly using OLEDs, LEDs or displays.

19. The illuminating apparatus of claim 15, wherein at least one of the deflectors provides a 0° illumination or a 2° illumination.

20. The illuminating apparatus of claim 15, wherein at least one of the deflectors is a deflecting prism or a partly transparent or semi-transparent mirror.

21. The illuminating apparatus of claim 15, which provides incident-light illumination, the illuminating light of which provides, by reflection on the retina, a combination of a red reflex and a dark field illumination in transmitted light.

22. A method for illuminating an eye in ophthalmic surgery, comprising:
   positioning at least one lens and at least one luminous field diaphragm on an illumination beam path;
   on the illumination beam path, guiding light from a light source through a main objective disposed between an optical deflector and the eye, onto the eye; and
   introducing into an illumination beam path a device for imaging a structure comprising transparent and non-transparent or opaque regions on or close to the retina of the eye,
   wherein the structure is configured as a pattern with concentric circles or comprises a grid pattern and/or checkerboard pattern elements.

23. A method for contrasting transparent media in a human eye in transmitted light, comprising:
   positioning at least one lens and at least one luminous field diaphragm on an illumination beam path;
   on the illumination beam path, guiding light from a light source through a main objective disposed between an optical deflector and the eye, onto the eye;
   acting with a structure upon the illumination beam path using a device that can be introduced into the illumination beam path; and
   imaging of the structure formed in the illumination beam path comprising transparent and non-transparent or opaque regions onto or close to the retina of the eye, for providing a structured red reflex,
   wherein the structure is configured as a pattern with concentric circles or comprises a grid pattern and/or checkerboard pattern elements.

* * * * *